(12) United States Patent
Ogilvie (10) Patent No.: US 7,891,813 B2
(45) Date of Patent: *Feb. 22, 2011

(54) VISION TESTING WITH RENDERED DIGITAL IMAGERY MODIFICATION UNDER VIEWER CONTROL

(76) Inventor: John W. Ogilvie, 1320 E. Laird Ave., Salt Lake City, UT (US) 84105

( * ) Notice: Subject to any disclaimer, the term of this patent is extended or adjusted under 35 U.S.C. 154(b) by 170 days.

This patent is subject to a terminal disclaimer.

(21) Appl. No.: 12/403,183

(22) Filed: Mar. 12, 2009

(65) Prior Publication Data

US 2009/0168020 A1 Jul. 2, 2009

Related U.S. Application Data

(63) Continuation of application No. 11/740,557, filed on Apr. 26, 2007, now Pat. No. 7,524,065.

(60) Provisional application No. 60/824,560, filed on Sep. 5, 2006.

(51) Int. Cl.
*A61B 3/02* (2006.01)

(52) U.S. Cl. .................................................... 351/222

(58) Field of Classification Search ................. 351/222, 351/223, 232, 237, 239, 241, 243, 205, 207, 351/210, 212, 216, 221
See application file for complete search history.

(56) References Cited

U.S. PATENT DOCUMENTS 7,275,830 B2 * 10/2007 Alster et al. ................. 351/223

* cited by examiner

*Primary Examiner*—Ricky L Mack
*Assistant Examiner*—Tuyen Q Tra
(74) *Attorney, Agent, or Firm*—Ogilvie Law Firm (57) ABSTRACT

Tools and techniques for vision testing alter refractive characteristics of rendered digital imagery and use feedback from a test subject to calculate information about errors in the subject's vision. Some embodiments produce a rendered digital image with vision-realistic rendering, present the test subject with the rendered digital image, accept input from the test subject and change the refractive sharpness of the rendered digital image in response to the input. Then they calculate refractive errors or other information about the test subject's vision based at least on: input from the test subject leading to a refractive sharpness change made during the changing step, and a refraction model which relates visual acuity to changes in the refractive sharpness of rendered digital imagery.

20 Claims, 3 Drawing Sheets

VISION TESTING WITH RENDERED DIGITAL IMAGERY MODIFICATION UNDER VIEWER CONTROL

RELATED APPLICATION

The present application is a continuation of application Ser. No. 11/740,557 filed Apr. 26, 2007, now U.S. Pat. No. 7,524,065, which claims priority to, and incorporates by reference, U. S. provisional patent application Ser. No. 60/824,560 filed Sep. 5, 2006.

BACKGROUND

A conventional refractor is an optical tool used by optometrists to help measure refractive errors in a person's vision. The person looks through the refractor at an image, as their optometrist selects lenses to place in the person's line of sight. The lenses may be made of glass or optical grade plastic. The refractor holds the lenses in a housing, and it helps organize the lenses in a way that lets the optometrist know which lense(s) the person is looking through to see the image, and what the refractive characteristics are of the chosen lenses. The person looks through the chosen lenses, and tells the optometrist whether a given choice of lenses in a sequence of lens choices makes the image appear more focused or less focused—the optometrist may repeatedly ask if the view through chosen lenses is "better or worse?" Thus, vision testing with a refractor is subjective, and proceeds in discrete lens-combining steps under the direct supervision of the optometrist. Refractors of this general type have been used for decades. For example, the U.S. trademark PHOROPTOR for eye-testing instruments for testing the refractive media and motor muscles of the eye was registered in 1922 (PHOROPTOR is a mark of Leica Microsystems Inc.).

More recently, autorefractors have been created. An autorefractor also includes lenses organized in a housing, but the choice of lenses to place in the person's line of sight is at least partially made by a computer program within the autorefractor. The person takes a seat and places their chin on a rest. One eye at a time, the person looks at a picture inside the autorefractor. The picture moves in and out of focus as the autorefractor places different lenses in the person's line of sight, while the autorefractor checks to see whether the corresponding image is in focus on the person's retina. Several readings can be automatically taken and averaged. No feedback is needed from the person; the testing is objective. However, it still proceeds in discrete lens combination steps with a relatively small number of lenses. With an autorefractor, an approximate measurement of a person's refractive error can be made quickly and automatically. However, it is not always as accurate as more labor-intensive and time-consuming tests, so an autorefractor measurement may be used merely as the starting point for the optometrist to perform a subjective refraction test using lenses in a manually controlled refractor as described above.

In short, a conventional refractor used for vision testing, such as a conventional autorefractor or a PHOROPTOR refractor, operates by changing the refraction in a beam of a sharp-edged source image until the image is perceived by the patient to be in focus, and then noting what change in refraction had to be added by the lenses to the patient's own optical refraction to obtain perceived focus. That added refraction change—the best-working lens combination—can then be replicated or at least approximated by eyeglasses or contact lenses, or by refractive surgery such as LASIK surgery.

It should be noted that the foregoing background was written in hindsight, with the present invention in mind. Thus, the particular cluster of ideas discussed in this background, or their characterization here, would not necessarily have been obvious to someone who did not have the benefit of familiarity with the invention.

SUMMARY

Some embodiments provide a vision testing system which presents a person with one or more rendered digital images. The vision testing system accepts input from the person, in response to which the system changes the refractive sharpness of the rendered digital image. The system calculates information about the person's vision based at least on: input from the person leading to a refractive sharpness change made during the changing step, and a refraction model which relates visual acuity to changes in the refractive sharpness of rendered digital imagery. Some embodiments use vision-realistic rendering based on aberration data to produce the rendered digital image.

More generally, some embodiments operate by changing the sharpness of a source image in a manner that uses digital processing to simulate refraction changes, without placing physical lenses between the source and the viewer to change the refraction in the image received by the viewer. The embodiment then analyzes the sequence of digital imagery refraction change requests (which indicate the viewer's subjective changes in sharpness and/or blurriness) to determine what effect would result from refraction changes made using corrective lenses.

Although many of the examples given herein are systems, the invention also provides other embodiments, such as methods and configured computer-readable storage media, for instance. The examples given are merely illustrative. This Summary is not intended to identify key features or essential features of the claimed subject matter, nor is it intended to be used to limit the scope of the claimed subject matter. Rather, this Summary is provided to introduce—in a simplified form—some concepts that are further described below in the Detailed Description. The present invention is defined by the claims, and to the extent this Summary conflicts with the claims, the claims should prevail. Other aspects of the present invention will become more fully apparent through the following description.

DESCRIPTION OF THE DRAWINGS

A more particular description of the invention will be given with reference to the attached drawings. These drawings only illustrate selected aspects of the invention and thus do not fully determine the invention's scope.

DETAILED DESCRIPTION

Definitions

Reference will now be made to exemplary embodiments such as those illustrated in the drawings, and specific language will be used herein to describe the same. But alterations and further modifications of the inventive features illustrated herein, and additional applications of the principles of the invention as illustrated herein, which would occur to one skilled in the relevant art(s) and having possession of this disclosure, should be considered within the scope of the invention.

In describing the invention, the meaning of terms is clarified, so the claims should be read with careful attention to these clarifications. Specific examples are given to illustrate aspects of the invention, but those of skill in the relevant art(s) will understand that other examples may also fall within the meaning of the terms used, and within the scope of one or more claims. Terms do not necessarily have the same meaning here that they have in general usage, in the usage of a particular industry, or in a particular dictionary or set of dictionaries. Reference numerals may be used with various phrasings, to help show the breadth of a term. The inventor asserts and exercises his right to provide his own lexicography. Terms may be defined, either explicitly or implicitly, here, elsewhere in the Detailed Description, and/or elsewhere in the application file.

Bearing this in mind, "vision-realistic rendering" is a computer science term of art, and hence is not open to arbitrary or overly general interpretation.

A "rendered digital image" is an image produced on a screen, monitor, or other display as the result of a rendering process. The rendering process is based on underlying pixel (or equivalently vector) data. The term "digital image" is used in contrast with images that are not susceptible to computational manipulations to achieve blurring or other effects discussed herein. A conventional eye chart printed on cardboard, for example, is not a digital image, although a digitization process could be used to create a digital image of such a chart.

A "device" could be made of hardware, software, or both.

The "refractive sharpness" of an image, or of a portion of an image, is the extent to which the potentially sharp image or image portion has been computationally blurred before being displayed. Such blurring may be done, for example, using a blur filter. "Blur filter" is a computer science term of art.

A "refractor interface" is an interface which provides control over simulated and/or actual lenses to interposition them, through physical movement and/or simulation, in between a source image and a viewer, thus altering the viewer's perceived image. Conventional autorefractors and PHOROPTOR refractors have refractor interfaces. A "software refractor interface" uses software in an embodiment to simulate a conventional refractor interface, which may make it easier for people familiar with conventional refractors to effectively operate embodiments that use fewer or no physical lenses.

Interrelation of Methods, Configured Media, and Systems

Figure 1:
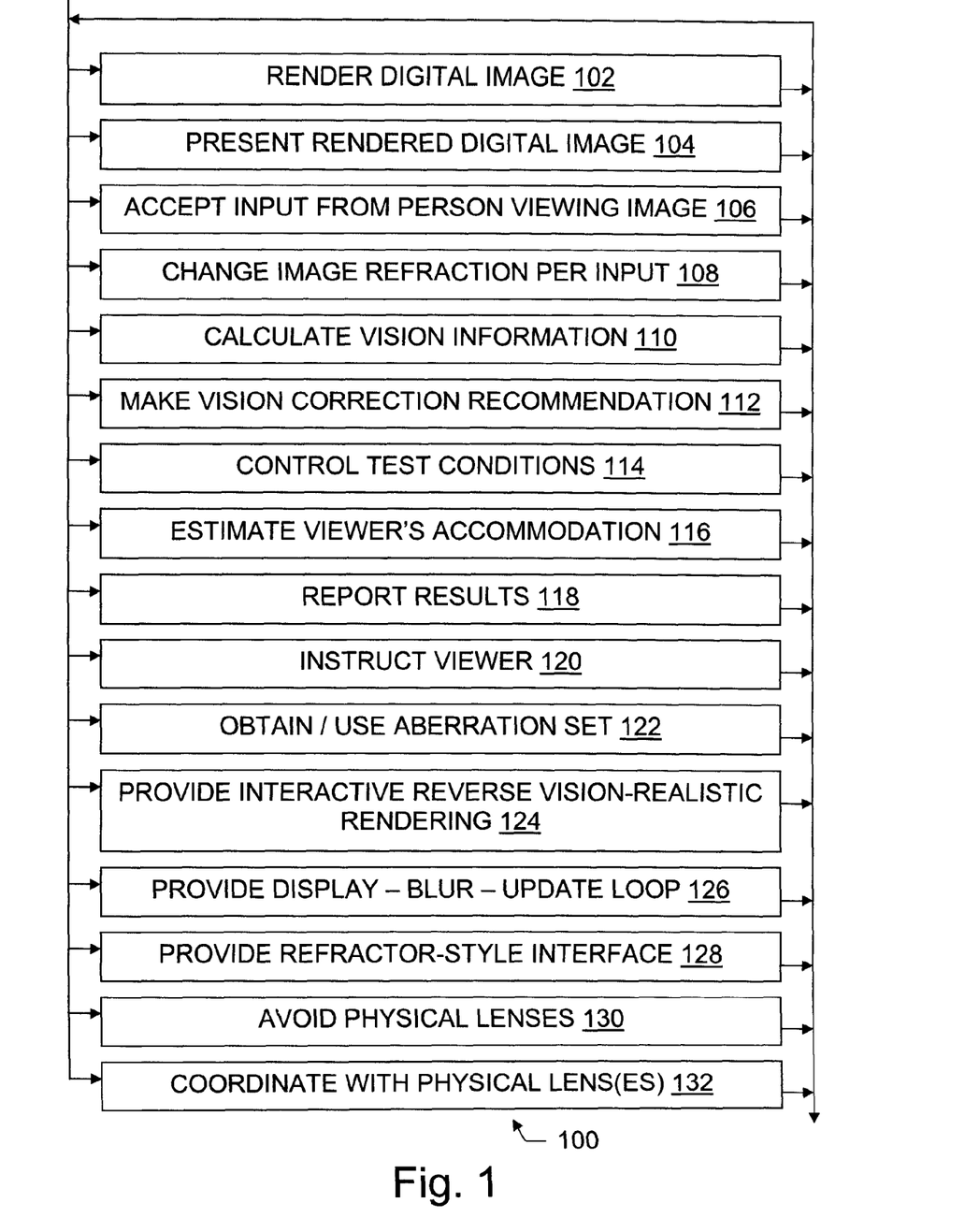
FIG. 1 is a flow chart illustrating steps of some method, configured storage medium, and other embodiments of the present invention.

FIG. 1 illustrates some method embodiments. However, not every step in the illustrated flowchart 100 need be included in a given embodiment exactly as shown. In a given embodiment, for example, zero or more illustrated steps may be repeated, perhaps with different parameters or data to operate on. Steps in an embodiment may also be done in a different order, omitted, combined, or otherwise depart from the illustrated flow, provided that the method performed is operable and conforms with at least one claim.

Figure 2:
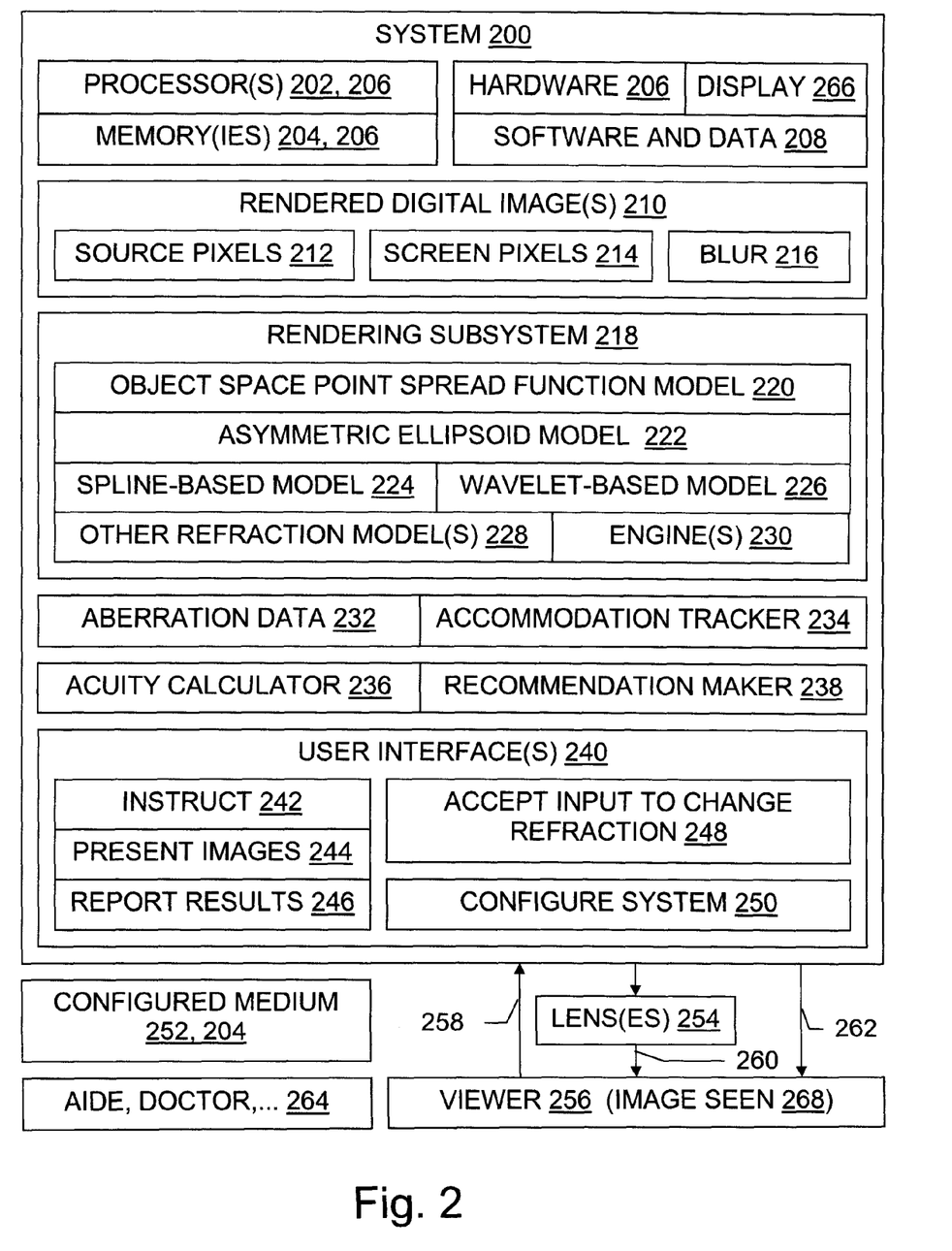
FIG. 2 is a block diagram illustrating some system and other embodiments of the present invention.

With reference to FIGS. 1 and 2, a computing system 200 embodiment includes hardware 206 and software 208. Processors 202 and memories 204 are examples of hardware 206. Other hardware 206 may include, for instance, user I/O devices typically found on digital devices (e.g., computers, PDAs, cell phones) such as keyboards, screens, touch screens, microphones, speakers, a mouse, a light pen, and so on; such devices may be part of a user interface 240. Other hardware 206 may also include disks (magnetic, optical, or otherwise), RAM, EEPROMS or other ROMs, and/or other configured storage media 252. Disks, CDs, flash modules, and the like are forms of memory 204. A memory 204 is a general-purpose storage medium; it may be removable or not, and it may be volatile or not. A memory 204 is configured with data and instructions 208 to thereby form a configured medium 252 which is capable of causing a system 200 that has a processor 202 to perform method steps disclosed herein. Accordingly, FIG. 1 helps illustrate configured storage media embodiments and system embodiments that perform the methods, as well as illustrating method embodiments.

A given system 200 may include a computer, a collection of communicating computers, another computing device such as a PDA or cell phone, and/or a combination of devices which have one or more processors 202 and cooperating memories 204. Not every item shown in FIG. 2 need be present in every system embodiment. Although the invention is illustrated in text and drawings by specific examples, other embodiments of the invention may depart from these examples. For instance, specific features of an example may be omitted, renamed, grouped differently, repeated, instantiated in hardware and/or software differently, or be a mix of features appearing in two or more of the examples.

EXAMPLES

One embodiment includes a computing device 200 having a display 266 in a user interface 240, a processor 202 operably connected with a memory 204, and software 208 configuring the memory and controlling the processor. This embodiment, and some others (e.g., some embodiments having multiple processors 202), operate by changing the sharpness of a source image in a manner that simulates refraction changes without actually placing physical lenses in the line of sight to change the refraction in the image before it reaches a viewer 256. These embodiments effectively propagate subjective changes in sharpness (and/or blurriness) by noting corresponding changes over time in the underlying source image data 212 to determine 110 what effect to viewer vision would result from changes in refraction. That is, whereas a conventional approach holds a source image constant and changes refraction by interposing lenses between the source image and the viewer, these embodiments change the source image itself in manner that simulates refraction changes caused by lenses.

A user interface 240 is implemented in some embodiments as software 208 running on conventional hardware, and in other embodiments as a combination of those two components with special purpose hardware that is used to replicate 128 more closely a conventional vision testing tool's interface. The illustrated interface 240 includes a visual display device 266 (computer screen, or a screen receiving projected digital rendered imagery, etc.) with supporting software 244 to present 104 rendered digital imagery for viewing. The illustrated interface 240 also includes user input hardware 206 (a keyboard, touch screen, mouse, light pen, microphone, etc. with supporting software) and software 248, 250 for accepting 106 blurring input and menu selections, etc., software 250 for configuring system data 208 such as stored patient data, network connectivity, natural language for use in instructions 120, software 242 for providing 120 operational instructions, and software 246 for reporting test results and/or reporting recommendations that are made based on calculations by an acuity calculator 236 and a recommendation maker 238.

During a rendering step 102, some embodiments render a digital image, that is, they apply a rendering process to source pixels 212 to produce screen pixels 214 which are shown to the viewer 256 on the display 266. Some systems 200 use vision-realistic rendering 102 based on a sequence of hypothetical patient data 232.

In some conventional vision-realistic rendering systems, actual patient data is gathered, e.g., by using a Shack-Hartmann device to gather aberration data from light emerging from a person's eye. See, e.g., Brian A. Barsky et al. "RAYS (Render As You See): Vision-Realistic Rendering Using Hartmann-Shack Wavefront Aberrations", www dot eecs dot Berkeley dot edu/~ddgarcia/optical/vrender/papers/psf.pdf, date unknown (per USPTO regulations this domain name is provided in a form not readily susceptible to confusion with a working hyperlink); Woojin Matthew Yu, "Simulation of Vision Through an Actual Human Optical System", M.S. Thesis, U.C. Berkeley, 2001; Brian A. Barsky, "Vision-Realistic Rendering: Simulation of the Scanned Foveal Image from Wavefront Data of Human Subjects", ACM Proceedings of $1^{st}$ Symposium on Applied perception in graphics and visualization, pp. 73-81, 2004. Actual patient aberration data could also be gathered using technology described in U.S. Pat. No. 6,761,454 to Lai, et al. The gathered aberration data are used to render an image which appears to a normally-sighted person as if they were viewing it through the vision of the person whose aberration data was used as a basis for the rendering. Vision-realistic rendering could be used, for instance, to generate images using the optics of various ophthalmic conditions such as cataracts, glaucoma, keratoconus, macular degeneration, and diplopia, to help educate doctors and patients about the effects of these visual defects.

By contrast, in some embodiments of the present invention an actual patient aberration data set need not be used. Instead, a sequence of hypothetical aberration data sets 232 is used, such that the hypothetical data sets plus the patient's aberration converge toward (and preferably result in) a specified perceived target image 268. Vision-realistic rendering 102 as used in these embodiments helps functionally define a rigorous mapping 220-228 between measurements of patient 256 vision aberration and displayed images 214. The embodiments provide (among other things) a rigorous mapping between displayed images 214 and perceived images. By utilizing vision-realistic rendering in reverse 124 in accordance with an embodiment, one can obtain data which rigorously lead to measurements of patent vision aberration. Vision-realistic rendering is used 124 "in reverse" in the sense that instead of starting with measurements of a human subject's vision aberrations, one ends up with such measurements 232.

Shack-Hartmann data 232 are only one way to help model or mathematically describe the refractive properties of the optical system of a person 256. Other models that can be used by a rendering subsystem 218 to control generation 102 of display images 214 can also be used in embodiments, when the model used provides some clinically useful measure of myopia, hyperopia, astigmatism, and/or other visual aberrations in a viewed image 268, in (or translatable to) diopters or another suitable unit.

In some embodiments, the model 220-228 is used by the rendering subsystem 218 to generate an initial display image 214, and the patient 256 is verbally given 120 a target image into which the patient converts 106, 108, 104 the display image, at least from the patient's perspective 268. The transformation of the initial display image 212/214 into a final display image 212/214 respectively, is measurable, and has meaning in terms of diopters or other aberration units. Because the final display image is perceived 268 as the specified 120 target image, but differs in the source space 212/214 from that target image, the extent to which the final display image differs from the target image is a measurement of the patient's visual aberration(s). That is, to the extent that the defect in viewer perception is a linear operator or else (like much refraction) can be adequately approximated 110 as being linear, the difference between the initial display image and the target image can be calculated 110 as the sum of the difference between the initial display image and the final display image, and the patient's aberration. Stated differently, an acuity calculator 236, 208 may calculate a target image by treating the initial displayed image as being modified by two filters, with one filter defined over time by patient manipulation 106 of the displayed images 214 through the user interface 240, and the other filter being provided by the patient's own eye(s):

(1) $\text{Display}_{initial} + (\text{Display}_{Final} - \text{Display}_{initial}) + \text{PatientAberration} = \text{TargetImage}$ or more simply:

(2) $\text{Display}_{Final} + \text{PatientAberration} = \text{TargetImage}$, so (3) $\text{PatientAberration} = \text{TargetImage} - \text{Display}_{Final}$ That is, to the extent that the target image and the final displayed image (which the patient perceives as close to or identical with the target image) can be described in meaningful optometric terms, their calculated 110 difference is a measure 208 of the patient's refractive error or other visual aberration.

Accordingly, mathematical models 220-228 of sight which are correlated with optometric measures, or which can be thus correlated analytically and/or empirically, and which are also useful in guiding computer graphic rendering engines 230, can be suitable for use in embodiments according to the present invention. Some vision-realistic rendering 218 uses Object Space Point Spread Functions in a mathematical model 220 of sight; see, e.g., the RAYS reference above. Other mathematical models of sight used in some embodiments 218 include an asymmetric ellipsoid model 222 described in Daniel D. Garcia et al, "CWhatUC: A Visual Acuity Simulator", Proceedings of SPIE, Volume 3246, Ophthalmic Technologies VIII, Pascal O. Rol, Karen M. Joos, Fabrice Manns, Editors, June 1998, pp. 290-298; a spline-based model 224 described in U.S. Pat. No. 6,241,355 to Barsky; a generalized imaging system model 228 described in Patrick Y. Maeda, et al., "Integrating Lens Design with Digital Camera Simulation", Proceedings of SPIE-IS&T Electronic Imaging, SPIE Vol. 5678, 2005; models 228 of blurring and other visual characteristics described in Brian A. Barsky, et al. "Camera Models and Optical Systems Used in Computer Graphics" (Part I and Part II), Proceedings of the 2003 International Conference on Computational Science and its Applications (ICCSA'03), Montreal, May 18-21, 2003, Second International Workshop on Computer Graphics and Geometric Modeling (CGGM'2003), Springer-Verlag Lecture Notes in Computer Science (LNCS), Berlin/Heidelberg, pages 246-265; and a model 226 of blurring described in Jaroslav Kautsky, et al., "A new wavelet-based measure of image focus", Pattern Recognition Letters 23 (2002) 1785-1794. The present invention is not, however, limited to any particular mathematical model of the human eye or any particular mathematical model of optical system characteristics.

One system 200 works as follows. A computer-generated scene is rendered 102, based on and/or otherwise corresponding to a hypothetical set of patient aberration measurements 232, e.g., a hypothetical Shack-Hartmann aberration data set for an eye having 20/20 vision. The scene 214 may show objects at different depths, may show three-dimensional objects, may have a specified (small to large) depth of field, and otherwise may have characteristics of interest in vision-realistic rendering.

The rendered scene 214 is displayed 104 to a user 256, and the user is instructed 120 to use a light pen 206 or other interface 240 tool to make all parts of the scene 214 equally blurry. In a variation, the viewer is instructed 256 to make two or more specified portions of a scene, or two scenes, equally blurry. As the user moves 106 the light pen over a given part of the scene, that part of the scene is blurred 108 with a blur filter 216 and re-rendered 102 and displayed 104, using vision-realistic rendering techniques and tools 230. The blur filter 216 correlates 110 sharpness changes 108 with optometric measures. That is, in coordination with the blurring 108, the hypothetical aberration data set 232 is updated. Those aberration data set readings could produce the corresponding blur in a conventional forward-operating vision-realistic rendering system. When the user is done blurring the image and causing corresponding aberration data set updates, this display-blur-update loop 126 is exited. The user 256 may be asked to expressly indicate when the user is done, e.g., by pressing a user interface 240 button or selecting an icon 240, or the system 200 may presume that the user is done if no further user input is received after some predetermined timeout period, e.g., ten seconds. Point spread functions 220 may be used in aberration data sets 232—as proxies for Shack-Hartmann data sets 232—in some embodiments.

Display-blur-update loops may also be provided 126 without using 124 reverse vision-realistic rendering, in embodiments which use refraction models 228 not reliant on a vision-realistic rendering engine 230. Recall that "vision-realistic rendering" is a computer science term of art. The term "display-blur-update loop", which was coined for use herein, encompasses loops in which blurring is done by vision-realistic rendering techniques as well as loops in which blurring is done by other rendering techniques.

The aberration data set 232 thus produced should correspond partly or fully to an actual aberration data set obtained contemporaneously by a Shack-Hartmann device for the same user eye(s). But the embodiment produces the aberration data set as just described, through an interactive reverse vision-realistic rendering loop 124, instead of obtaining the aberration data set by use of a Shack-Hartmann device. However, it may be helpful for clinical tests and/or for calibration to sometimes produce aberration data sets for one or more subjects 256 in both ways—by interactive reverse vision-realistic rendering 124, and by actual Shack-Hartmann device measurements—and to then compare 236 those data sets. The mapping between corrective prescriptions and Shack-Hartmann aberration data sets can then be used by software 238 to produce 112 a corrective prescription for the user 256 from the aberration data set 232 that was obtained 122 by interactive reverse vision-realistic rendering.

The phenomenon of viewer accommodation to blurriness is known. See, e.g., Michael A. Webster et al., "Neural adjustments to image blur", Nature Neuroscience, volume 5 no. 9, pp. 839-840, September 2002. Some embodiments include software 234 to measure 116 and compensate 108 for accommodation effects. In one system 200, the user 256 is presented 104 a first displayed image 214, and guided through blurring 106, 108 of at least portions of that image to obtain an aberration data set 232 as described above. Then a second displayed image 214 is displayed 104. This second image is blurred 216 a measured quantum more than the first displayed image. The blurring quantum may be determined by software 234 using vision-realistic techniques per Barsky, for instance, or camera autofocusation measures per Kautsky. The user 256 is guided through blurring of at least a portion of the second image to obtain a second aberration data set 232. A third, further blurred image is displayed, and a third aberration data set is obtained 232. A calculated 116 trend in blurring should then match the trend in aberration 232. It may also be determined experimentally whether these trends are linear or conform with some other specified mathematical relationship, which can then be used to estimate 116 viewer accommodation. Regardless, they provide data which show the progress of a viewer's accommodation over time, and which can be read in reverse time and in correlation with the aberration data sets to obtain 116 an aberration data set 232 matching a point having zero (or acceptably small) accommodation.

In this example, three blur values and corresponding aberration sets are used in estimating 116 accommodation, but in other embodiments fewer or more blur values, and fewer or more display images, for example, can be used. The blurriness of display images 214 could also be held constant by the accommodation estimation module 234, for instance, instead of being increased. Blurriness could also be decreased by sharpening images to be displayed. Indeed, negative changes to blurriness (that is, having the rendering subsystem 218 increase sharpness per Webster et al. or otherwise) could be done in any of the embodiments discussed above, in place of or in addition to, positive changes to blurriness, that is, changes that increase blurriness.

Some embodiments control 114 testing conditions to influence factors of the type known now or subsequently developed, in optometry. For instance, some embodiments control 114 the distance between a patient's eyes and a display device 266, e.g., by having a test aide 264 place the patient's chin on a rest or by instructing 120 the patient 256 to place their forehead against a rest, in a manner similar to that done when using a conventional refractor or conventional autorefractor. Some embodiments control 114 the lighting conditions, e.g., by giving 120 the optometrist 264 or the patient 256 instructions for lowering ambient environment lights and/or for dilating the patient's pupils. Some embodiments use test patterns 214, at a variety of expected levels of focus and/or in different apparent or actual positions, in order to obtain 106 test results which can then be averaged 110, cross-referenced 110 against one another, or otherwise used 110 to improve vision test accuracy and/or reliability. Such testing condition controls 114 can be used to help provide 118 reproducible results and/or to calibrate the system 200 with the particular patient 256.

Some embodiments completely avoid 130 the use of physical lenses, including lens sets like those used in conventional refractors and conventional autorefractors. That is, the line of sight 262 from the display 266 and its rendered digital image 214 to the eyes of the viewer 256 does not go through any physical (i.e., glass, optical grade plastic, fluid) lens, at least not as an intended part of the system 200 design and operation. Other embodiments coordinate 132 the blurring 216 and/or other refraction changes 108 made by the software 208 with those made by physical refraction lenses 254; the line of sight 260 in these cases goes from the system display 266 through one or more physical lenses 254 to the viewer's eyes.

Accordingly, not every embodiment requires use of corrective lenses 254. That is, a system 200 may include, but does not always require, a lens-based subjective refractor component and/or a lens-based autorefractor component. It is contemplated that specific and useful information may be obtained about the nature and extent of a person's refractive errors, for example, without 130 any such use of corrective lenses. However, no prototype of the present invention has been implemented at this point, nor has any clinical testing of it been done. Accordingly, some embodiments of the present invention may be commercially or otherwise well suited for use in conjunction 132 with conventional vision testing tools and techniques that use corrective lenses 254. In particular and without excluding other uses, a given embodiment may be used for initial tests, similar to the way conventional autorefractors are often used, with the results 118 of those initial tests guiding the optometrist 264 in selecting lenses for use in a conventional subjective refractor test.

To facilitate ease of use by optometrists 264, technicians 264, and others who are familiar with the operation of conventional refractors and conventional autorefractors, some embodiments provide 128 a refractor-style interface. This interface 240 may take the form of conventional hardware (knobs, levers, etc.) interfaced with software 208 via switches, pressure sensors, and the like. Alternately, some or all of the interface 240 may visually and operationally replicate 128 the conventional interface hardware on a screen 266, as a flight simulator for example replicates visually and operationally on a screen the hardware found in an airplane cockpit.

Not every embodiment need have a refractor-style interface. For instance, software embodiments may avoid or supplement the discrete lens combinations of a refractor-style interface in order to provide much smoother changes 108 in image 214 refraction than is possible in a perceived image using movements of physical lenses. Accordingly, some embodiments depart from the discrete refraction changes inherent in conventional refractor interfaces, by providing continuous changes using a slider bar, wheel rotation, or other interface 240 element for smoothly controlled continuous change, or at least change that appears to users as continuous. Instead of being asked to distinguish refracted images as "better or worse" the viewer 256 may be asked 120 to stop when the image 268 is in focus. Moreover, the effective number of blurrings 216 possible (and hence the number of different perceived images 268) is much larger in some embodiments than the number of lenses used in a conventional refractor or a conventional autorefractor, because changes are made to the source image 214 rather than being made merely by interposing physical lenses.

ADDITIONAL EXAMPLES

One system 200 includes a computing device having a display 266, a user interface 240, a processor 202 operably connected with a memory 204, and software 208 and user test data 208 configuring the memory and controlling the processor. In operation, this system displays 104 a pattern 214 to a user 256; this is the "initial displayed pattern". The user 256 sees 258 a resultant pattern, but due to refraction errors and/or other flaws in the user's visual organs, the pattern 268 seen by the user (the "initial perceived pattern") is not precisely the same as the initial displayed pattern 214. For instance, the initial perceived pattern 268 may be blurred, spatially warped, or chromatically warped or shifted, may contain artifacts not displayed, or may otherwise differ from the initial displayed pattern, depending on the nature of the problems with the user's vision. Common refractive errors include spherical errors and cylindrical errors, but the present invention is not limited to testing only for such errors.

The user 256 is then instructed 120 as to a target pattern. These instructions may be written, spoken, or symbolic, for example. For instance, the user may be instructed 120 to "place all the dots in a straight line going from left to right across the middle of the display", or to "make each part of the picture equally blurry, using a 'blur-wand' touched to the screen". In response, the user interacts 106, 260/262 with the system to change 108 the displayed image. This results in a "subsequent displayed pattern" 214 having changed pixel coordinates 212, changed blurriness values 216, etc. in system memory, and therefore also results in a new "subsequent perceived pattern" that is the subsequent displayed pattern as seen by the user. For convenience, the various attributes of a pattern, such as source pixel data, camera position, lighting values and position, blurriness filters, and so on, may be conceptually grouped and treated as a single rendered digital image 210, but as noted these and other components may be organized differently in different embodiments. By combining 110 the objective changes in pixel positions, blurriness, etc. in the system memory with a target instruction template 208 representing the subjective change the user 256 was instructed to seek (and also assuming good faith and some competence on the user's part), the vision testing system obtains 110 information about the nature of the user's vision errors.

Figure 3:
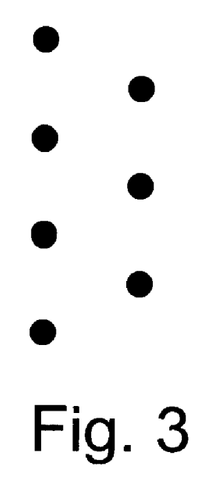
FIG. 3 shows an example displayed pattern, which is presented on a display to a viewer as a starting point in a vision test.

As a simple example, suppose that the initial displayed pattern includes seven dots equally spaced as shown in FIG. 3. The user 256 is instructed 120 to "place the dots in a vertical line, equally spaced apart". The user moves 106 the dots about, using a mouse, light pen, touch screen, or the like. The user produces the subsequent displayed pattern shown in FIG. 4, because the user sees 262 that pattern—through the user's own vision system—as the subsequent perceived pattern shown in FIG. 5. That is, to the user it appears that the target pattern has been achieved. In this case, the target displayed pattern and the perceived pattern match, so FIG. 5 is also the template 208 for the target pattern. The difference between FIG. 4 and the target template in FIG. 5 indicates 110 that the user 256 has a refractive error which maps the second dot from the top from the displayed position to the perceived position. It also provides 118 a measure of that refractive error, for use in prescribing corrective lenses or corrective surgery.

Figure 4:
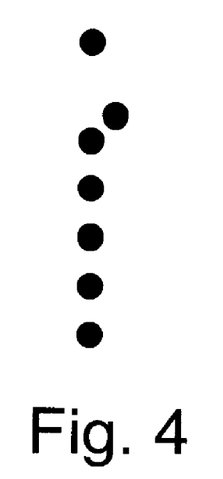
FIG. 4 shows a subsequent displayed pattern which could be produced by the viewer from the example pattern shown in FIG. 3.
Figure 5:
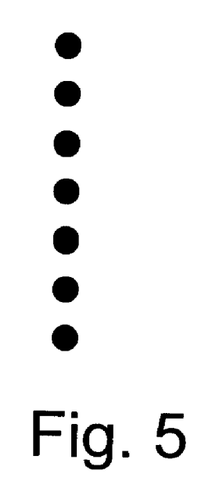
FIG. 5 shows the displayed pattern of FIG. 4 as it is perceived by the viewer.
Figure 6:
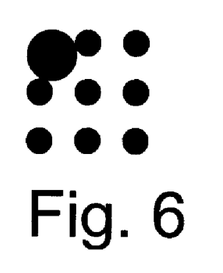
FIG. 6 shows another example displayed pattern, which is presented on a display to a viewer as a starting point in a vision test.
Figure 7:
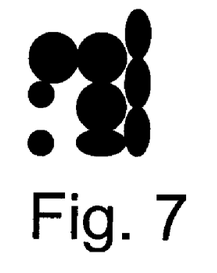
FIG. 7 shows a subsequent displayed pattern which could be produced by the viewer from the example pattern shown in FIG. 6.
Figure 8:
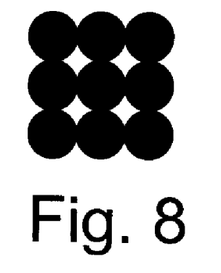
FIG. 8 shows the displayed pattern of FIG. 7 as it is perceived by the viewer in question.

As yet another example, consider a system 200 that has main components as in the example involving FIGS. 3 through 5, which operates by obtaining information about vision errors based on the difference between initial and subsequent displayed patterns and on the target template. In this example, the system 200 presents an initial displayed pattern 214 that includes a grid of pixels represented in FIG. 6. The user 256 is instructed 120 to "make all parts of the image equally blurry". The user blurs 106 parts of the image using a light pen 206 as a blurring paintbrush 216 (e.g., as in the commercially available Adobe PhotoShop program, although other blur filters 216 may be used to provide a more rigorous and quantified correspondence 228 between blur results and underlying refractive error causes). The user produces the subsequent displayed pattern shown in FIG. 7, because the user sees 262 that pattern—through the user's own vision system—as the subsequent perceived pattern shown in FIG. 8. FIG. 8 is also the template 208 for the target pattern. The difference between FIG. 7 and the target template in FIG. 8 indicates 110 that the user has a refractive error which blurs the bottom two thirds of the leftmost column of pixels, and which partially blurs the rightmost column of pixels and the center bottom row pixel, as indicated. That is, because the user sees FIG. 8 as the perceived image 268 when given 104 FIG. 7 as an input, the software can determine 110 that blurring not already done in FIG. 7 must be coming from the user's own vision system.

Conventional vision testing, especially for refraction errors, often starts with a user view of some item, and then tries to improve the user's view by changing the optical path, e.g., by inserting lenses between the user and the item to change refraction. Some embodiments of the present invention start with a user view, and then try to make parts of that view worse, e.g., by making the perceived view uniformly blurry by having the user blur parts of the view that are not perceived as sufficiently blurry. Then the embodiment determines 110 refractive errors based on the target image and the user's changes—the areas the user changed 106 less or not at all are those already blurred by the user's own optics. That is, the embodiment asks the user 256 to change the perceived quality 268 of the view, not necessarily to improve that perceived quality.

CONCLUSION

Although particular embodiments of the present invention are expressly illustrated and described herein as methods or systems, it will be appreciated that discussion of one type of embodiment also generally extends to other embodiment types. For instance, the descriptions of methods in connection with FIG. 1 also help describe systems like those described in connection with FIG. 2, and vice versa. It does not follow that limitations from one embodiment are necessarily read into another.

The invention may be embodied in various ways, e.g., with processes and/or hardware on a server computer, on a client or peer, or on a standalone computer, software (data instructions) in RAM or permanent storage for performing a method, general purpose computer hardware configured by software, special-purpose computer hardware, listing reports or other data produced by a method, and so on.

Reference has been made to the figures throughout by reference numerals. Any apparent inconsistencies in the phrasing associated with a given reference numeral, in the figures or in the text, should be understood as simply broadening the scope of what is referenced by that numeral.

As used herein, terms such as "a" and "the" are inclusive of one or more of the indicated item or step. In particular, in the claims a reference to an item generally means at least one such item is present and a reference to a step means at least one instance of the step is performed.

Headings are for convenience only; information on a given topic may be found outside the section whose heading indicates that topic.

All claims as filed are part of the specification and thus help describe the invention, and repeated claim language may be inserted outside the claims as needed.

While the present invention has been shown in the drawings and described above in connection with exemplary embodiments of the invention, it will be apparent to those of ordinary skill in the art that numerous modifications can be made without departing from the principles and concepts of the invention as set forth in the claims. Although the subject matter is described in language specific to structural features and/or methodological acts, it is to be understood that the subject matter defined in the appended claims is not necessarily limited to the specific features or acts described above the claims. It is not necessary for every means or aspect identified in a given definition or example to be present or to be utilized in every embodiment of the invention. Rather, the specific features and acts described are disclosed as examples for consideration when implementing the claims.

The scope of the invention is indicated by the appended claims rather than by the foregoing description. All changes which come within the meaning and range of equivalency of the claims are to be embraced within their scope to the full extent permitted by law.

What is claimed is:

1. A method comprising:
   using vision-realistic rendering based on aberration data to produce a rendered digital image;
   presenting a person with the rendered digital image;
   accepting input from the person, through at least one of the following: a touch screen, a light pen;
   changing the refractive sharpness of the rendered digital image in response to input accepted from the person; and
   calculating information about the person's vision based at least on: input from the person leading to a refractive sharpness change made during the changing step, and a refraction model which relates visual acuity to changes in the refractive sharpness of rendered digital imagery.

2. The method of claim 1, further comprising a rendering step which uses vision-realistic rendering that employs at least one of the following: object space point spread functions, an asymmetric ellipsoid model of vision, a spline-based model of vision, a wavelet-based model of vision.

3. The method of claim 1, wherein the method provides the person with a display-blur-update loop.

4. The method of claim 1, further comprising a blur challenging step which instructs the person to use an interface tool to make specified portions of the rendered digital image equally blurry.

5. The method of claim 1, wherein the presenting step presents the rendered digital image in a software refractor interface, and the accepting step accepts input from the person through the software refractor interface.

6. The method of claim 1, further comprising obtaining a plurality of aberration sets which depend on input from the person and on the refraction model.

7. The method of claim 6, further comprising the step of estimating the person's accommodation to blurriness based on at least one of the aberration sets.

8. The method of claim 1, further comprising refracting the rendered digital image through a physical lens before presenting the image to the person, and using a refraction characteristic of the physical lens in calculating information about the person's vision.

9. A method comprising:
   producing, through vision-realistic rendering, a rendered digital image, wherein the producing step uses vision-realistic rendering based on at least one of the following to produce the rendered digital image: hypothetical aberration data, gathered actual patient aberration data;
   presenting a person with the rendered digital image at a controlled distance;
   accepting, through a device, input from the person;
   changing the refractive sharpness of the rendered digital image in response to input accepted from the person; and calculating information about the person's vision based at least on: input from the person leading to a refractive sharpness change made during the changing step, and a refraction model which relates visual acuity to changes in the refractive sharpness of rendered digital imagery.

10. The method of claim 9, wherein the changing step changes the refractive sharpness of only part of the rendered digital image.

11. The method of claim 9, wherein the method provides the person with interactive reverse vision-realistic rendering.

12. The method of claim 9, wherein the calculating step calculates a vision correction recommendation, and the method further comprises reporting the vision correction recommendation.

13. The method of claim 9, further comprising refracting the rendered digital image through a physical lens before presenting the image to the person, and using a refraction characteristic of the physical lens in calculating information about the person's vision.

14. A system, comprising:
   multiple processors in operable connection with at least one memory;
   the processors configured by data and instructions to perform the following:
      produce, through vision-realistic rendering, a rendered digital image;
      present a person with the rendered digital image;
      accept, through a device, input from the person;
      change the refractive sharpness of the rendered digital image in response to input accepted from the person;
      obtain a plurality of aberration sets which depend on input from the person and on a refraction model which relates visual acuity to changes in the refractive sharpness of rendered digital imagery;
      estimate the person's accommodation to blurriness based on at least one of the aberration sets; and
      calculate information about the person's vision based at least on: input from the person leading to a refractive sharpness change made during the changing step, and the refraction model.

15. The system of claim 14, wherein the aberration sets comprise a sequence of hypothetical aberration data sets used to calculate information about the person's vision.

16. The system of claim 14, wherein the system provides the person with interactive control of blurriness in presented rendered digital imagery.

17. The system of claim 14, wherein the system accepts input through a software refractor interface.

18. The system of claim 14, wherein the system is free of physical lenses interposed between the rendered digital imagery and the person's eyes.

19. The system of claim 14, further comprising a physical lens which refracts the rendered digital image, and wherein a refraction characteristic of the physical lens is used in calculating information about the person's vision.

20. The system of claim 14, further comprising a means for measuring the person's accommodation to blurriness.

* * * * *